US011210809B2

United States Patent
Matsuura

(10) Patent No.: US 11,210,809 B2
(45) Date of Patent: Dec. 28, 2021

(54) IMAGE PROCESSING APPARATUS, IMAGE DETERMINATION METHOD AND NON-TRANSITORY COMPUTER-READABLE STORAGE MEDIUM

(71) Applicant: CANON KABUSHIKI KAISHA, Tokyo (JP)

(72) Inventor: Tomohiko Matsuura, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/902,686

(22) Filed: Jun. 16, 2020

(65) Prior Publication Data
US 2020/0311975 A1 Oct. 1, 2020

Related U.S. Application Data

(63) Continuation of application No. PCT/JP2018/041320, filed on Nov. 7, 2018.

(30) Foreign Application Priority Data

Dec. 27, 2017 (JP) .............................. JP2017-252067

(51) Int. Cl.
*G06T 7/00* (2017.01)
*G06T 7/73* (2017.01)
*A61B 6/00* (2006.01)
*G06K 9/00* (2006.01)
*G06T 3/40* (2006.01)

(52) U.S. Cl.
CPC .............. *G06T 7/74* (2017.01); *A61B 6/5217* (2013.01); *G06K 9/00362* (2013.01); *G06T 3/4038* (2013.01); *G06T 2207/10116* (2013.01); *G06T 2207/20021* (2013.01); *G06T 2207/20081* (2013.01); *G06T 2207/20221* (2013.01); *G06T 2207/30196* (2013.01)

(58) Field of Classification Search
None
See application file for complete search history.

(56) References Cited

U.S. PATENT DOCUMENTS

| | | | |
|---|---|---|---|
| 7,327,823 B2 | 2/2008 | Matsuura | |
| 8,229,067 B2* | 7/2012 | Matsuura | ................. H04N 5/32 378/62 |
| 8,340,383 B2 | 12/2012 | Matsuura | |
| 9,691,150 B2* | 6/2017 | Miyasa | ................... G06T 11/60 |

(Continued)

FOREIGN PATENT DOCUMENTS

| | | |
|---|---|---|
| JP | 2000-157519 A | 6/2000 |
| JP | 2000-258861 | 9/2000 |

(Continued)

*Primary Examiner* — Delomia L Gilliard
(74) *Attorney, Agent, or Firm* — Venable LLP

(57) ABSTRACT

An image processing apparatus obtains a plurality of radiation images generated by causing a plurality of radiation detectors to detect radiation with which a subject is irradiated, and generates an elongated image by synthesizing the plurality of radiation images. The image processing apparatus estimates a direction of the subject in each of the plurality of radiation images, and determines a direction of the subject in the elongated image based on a direction estimation result on each of the plurality of radiation images.

20 Claims, 9 Drawing Sheets

(56) References Cited

U.S. PATENT DOCUMENTS

| | | | |
|---|---|---|---|
| 9,877,693 B2 | 1/2018 | Toyoda et al. | |
| 2003/0185426 A1* | 10/2003 | Ohishi | G06T 19/00 382/128 |
| 2007/0030957 A1* | 2/2007 | Pommi | G06T 7/73 378/197 |
| 2008/0292048 A1 | 11/2008 | Haras | |
| 2013/0148779 A1* | 6/2013 | Notohara | A61B 6/4085 378/22 |
| 2015/0351709 A1* | 12/2015 | Dirauf | A61B 6/0492 378/206 |
| 2016/0302752 A1* | 10/2016 | Ito | G06K 9/60 |
| 2016/0302753 A1* | 10/2016 | Suzuki | A61B 6/56 |
| 2018/0357762 A1* | 12/2018 | Kobayashi | A61B 6/025 |

FOREIGN PATENT DOCUMENTS

| | | |
|---|---|---|
| JP | 2002-085392 | 3/2002 |
| JP | 2005-202477 | 7/2005 |
| JP | 2007-229246 A | 9/2007 |
| JP | 2008-67916 A | 3/2008 |
| JP | 2012-040140 | 3/2012 |
| JP | 2012-045172 | 3/2012 |
| JP | 2016-076843 | 5/2016 |
| WO | 2015/045005 | 4/2015 |

* cited by examiner

IMAGE PROCESSING APPARATUS, IMAGE DETERMINATION METHOD AND NON-TRANSITORY COMPUTER-READABLE STORAGE MEDIUM

CROSS-REFERENCE TO RELATED APPLICATIONS

This application is a Continuation of International Patent Application No. PCT/JP2018/041320, filed Nov. 7, 2018, which claims the benefit of Japanese Patent Application No. 2017-252067, filed Dec. 27, 2017, both of which are hereby incorporated by reference herein in their entirety.

BACKGROUND

Field of the Invention

The present invention relates to an image processing apparatus that processes a radiation image obtained by radiation, a control method for the image processing apparatus, and a radiation imaging apparatus including the image processing apparatus.

Background Art

In the field of medical radiation imaging, radiation imaging aimed at a wide observation region such as the spine or lower extremity of a subject is called elongated imaging, and a radiation image obtained by elongated imaging is called an elongated image. PTL 1 discloses a radiation imaging system that performs elongated imaging by using a plurality of radiation detectors arranged side by side. In this radiation imaging system, a plurality of radiation detectors obtain a plurality of radiation images (partial images), and an image processing apparatus synthesizes the plurality of radiation images, thereby generating one radiation image (elongated image) depicting an overall wide observation range. Each of the plurality of radiation detectors used in this radiation imaging system is a portable radiation detector. This makes it possible to selectively use such radiation imaging apparatuses such that a plurality of radiation imaging apparatuses are installed on a gantry dedicated to elongated imaging to perform elongated imaging or one radiation imaging apparatus is detached from the gantry to perform general imaging.

Making it possible to detach and selectively use each radiation detector may change the placement (placement order and orientations) of radiation detectors at the time of elongated imaging. In such a case, the placement order and orientations of partial images output from the plurality of radiation detectors also change. Accordingly, an elongated image cannot be properly generated without considering this case. PTL 2 discloses a method of performing imaging upon overlapping end portions of adjacent radiation detectors, and synthesizing obtained images upon determining the placement order of the images based on the similarities of end portions of the images.

CITATION LIST

Patent Literature

PTL 1: Japanese Patent Laid-Open No. 2012-040140
PTL 2: Japanese Patent Laid-Open No. 2012-045172

In radiation imaging in general, an obtained image is required to be displayed on a screen in an up-down direction suitable for diagnosis. This applies to images obtained by elongated imaging. For example, in imaging of the trunk region such as the chest region or the abdominal region, an obtained image is generally displayed on a screen with the head side of the subject being oriented in the upper direction. According to PTL 2, although it is possible to generate an elongated image by properly connecting a plurality of images, it is not possible to determine the direction of the subject in the elongated image. In order to cope with such a problem, a gravity sensor capable of detecting a gravity direction may be provided to decide the up-down direction of an image based on the detected gravity direction. However, in elongated imaging using a plurality of portable radiation detectors described above, when detection results concerning the up-down directions of the respective radiation detectors differ from each other, the up-down direction of the elongated image cannot be decided.

It is desired for the elongated image obtained by elongated imaging using a plurality of radiation detectors to allow accurate determination of the direction of the subject.

SUMMARY

According to one aspect of the present invention, there is provided an image processing apparatus comprising: an obtaining unit configured to obtain a plurality of radiation images generated by causing a plurality of radiation detectors to detect radiation with which a subject is irradiated; a synthesizing unit configured to generate an elongated image by synthesizing the plurality of radiation images; an estimation unit configured to estimate a direction of the subject in each of the plurality of radiation images; and a determination unit configured to determine a direction of the subject in the elongated image based on a direction estimation result obtained by the estimation unit on each of the plurality of radiation images.

According to another aspect of the present invention, there is provided an image determination method comprising: obtaining a plurality of radiation images by detecting radiation with which a subject is irradiated; generating an elongated image by synthesizing the plurality of radiation images; estimating a direction of the subject in each of the plurality of radiation images; and determining a direction of the subject in the elongated image based on a direction estimation result obtained in the estimating on each of the plurality of radiation images.

According to another aspect of the present invention, there is provided a non-transitory computer-readable storage medium storing a program for causing a computer to execute an image determination method comprising: obtaining a plurality of radiation images by detecting radiation with which a subject is irradiated; generating an elongated image by synthesizing the plurality of radiation images; estimating a direction of the subject in each of the plurality of radiation images; and determining a direction of the subject in the elongated image based on a direction estimation result obtained in the estimating on each of the plurality of radiation images.

Further features of the present invention will become apparent from the following description of exemplary embodiments with reference to the attached drawings.

DESCRIPTION OF THE EMBODIMENTS

A radiation imaging apparatus according to an embodiment will be described in detail below with reference to the accompanying drawings. The following will exemplify a radiation detector using an indirect FPD that converts applied radiation into visible light through a phosphor (scintillator) and detects the obtained visible light through a photodiode, thereby performing radiation imaging. Obviously, however, this detector can be applied to a direct FPD that directly converts radiation into electrons. Note that FPD stands for flat panel detector.

First Embodiment

Figure 1:
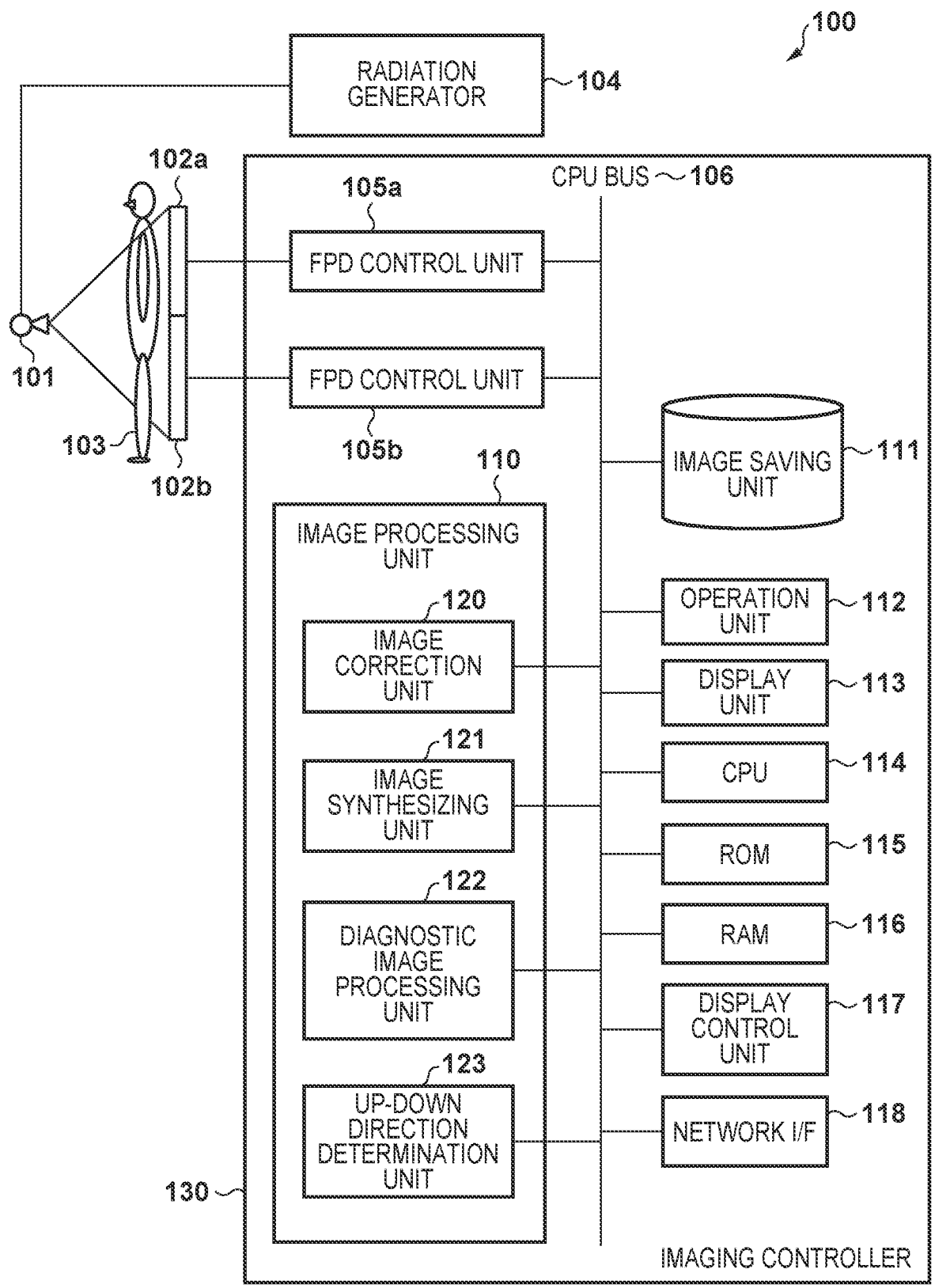
FIG. 1 is a block diagram showing an example of the arrangement of a radiation imaging apparatus according to an embodiment.

FIG. 1 shows the functional arrangement of a radiation imaging apparatus 100 according to this embodiment. The radiation imaging apparatus 100 includes a radiation generating unit 101, a radiation generator 104, and an imaging controller 130. The radiation generating unit 101 irradiates a subject 103 with radiation. The radiation generator 104 supplies a high-voltage pulse to the radiation generating unit 101 to generate radiation in accordance with the pressing of an exposure switch (not shown). FPDs 102a and 102b as a plurality of radiation detectors each convert radiation passing through the subject 103 into visible light through the phosphor, detect the converted visible light through the photodiode, and obtain an analog electrical signal. The analog electrical signals detected by the FPDs 102a and 102b are converted (A/D-converted) into digital data and transmitted as image data to FPD control units 105a and 105b. This embodiment will exemplify a case in which elongated imaging is performed by using two sets of FPDs 102 and FPD control units 105.

In the imaging controller 130 as an image processing apparatus, the FPD control units 105a and 105b are connected to a CPU bus 106. The following will show an arrangement in which one computer (CPU 114) is connected to the CPU bus 106. However, a plurality of computers may be connected to the CPU bus 106. The FPD control units 105a and 105b are an example of an obtaining unit that obtains a plurality of radiation images generated by causing a plurality of radiation detectors to detect radiation with which a subject is irradiated. The obtaining unit is not limited to this. For example, this embodiment may use an arrangement configured to obtain a radiation image from an HIS or RIS via a network I/F 118 (to be described later). In this case, HIS stands for hospital information systems, and RIS stands for radiology information systems.

An image processing unit 110, an image saving unit 111, an operation unit 112, and a display unit 113 are further connected to the CPU bus 106. In addition, a CPU 114, a ROM 115, a RAM 116, a display control unit 117, the network I/F 118, and the like, which are provided in a general computer, are connected to the CPU bus 106. The CPU 114 is a central processing unit, which controls the overall imaging controller 130 by executing programs stored in the ROM 115 or the RAM 116. The ROM 115 is a non-volatile read only memory, which stores various programs executed by the CPU 114 and various data. The RAM 116 is a volatile random access memory that can be read and written at any time. The RAM 116 provides a work area used by the CPU 114. The display control unit 117 causes the display unit 113 to perform various types of display operations under the control of the CPU 114. For example, the display control unit 117 displays an elongated image on the display unit 113 based on the direction of a subject determined by an up-down direction determination unit 123. The network I/F 118 connects the imaging controller 130 to a network. The radiation imaging apparatus 100 is connected to an information system, for example, an HIS or RIS, via the network I/F 118.

The image processing unit 110 includes an image correction unit 120, an image synthesizing unit 121, a diagnostic image processing unit 122, and the up-down direction determination unit 123. The image correction unit 120 performs various types of correction processing, so-called preprocessing, such as offset correction, sensitivity correction, and defective pixel correction, which are performed to correct characteristic variations of solid-state image sensors of the FPDs 102a and 102b. The image synthesizing unit 121 generates an elongated image by synthesizing a plurality of radiation images. In this embodiment, the image synthesizing unit 121 generates an elongated image by synthesizing a plurality of radiation images obtained by a plurality of FPDs (FPDs 102a and 102b). The diagnostic image processing unit 122 performs diagnostic image processing such as gray level processing, dynamic range processing, and spatial frequency processing. The up-down direction determination unit 123 determines the up-down direction of a subject in an elongated image as an obtained image by image determination. The up-down direction determination unit 123 will be described in more detail with reference to FIG. 8. Note that the image processing unit 110 may be implemented by causing the CPU 114 to execute predetermined programs or may be partly or entirely implemented by dedicated hardware.

The image saving unit 111 is a large-capacity storage device that saves radiation images output from the FPD control units 105a and 105b and radiation images processed by the image processing unit 110. The operation unit 112 inputs user instructions to the image processing unit 110 and the FPD control units 105a and 105b. The display unit 113 displays, for example, the elongated image generated by the image processing unit 110 under the control of the display control unit 117. At this time, the display control unit 117 controls, for example, the display direction of an elongated image so as to make the head region of a subject be oriented upward in accordance with the up-down direction determination result obtained by the up-down direction determination unit 123.

Figure 2:
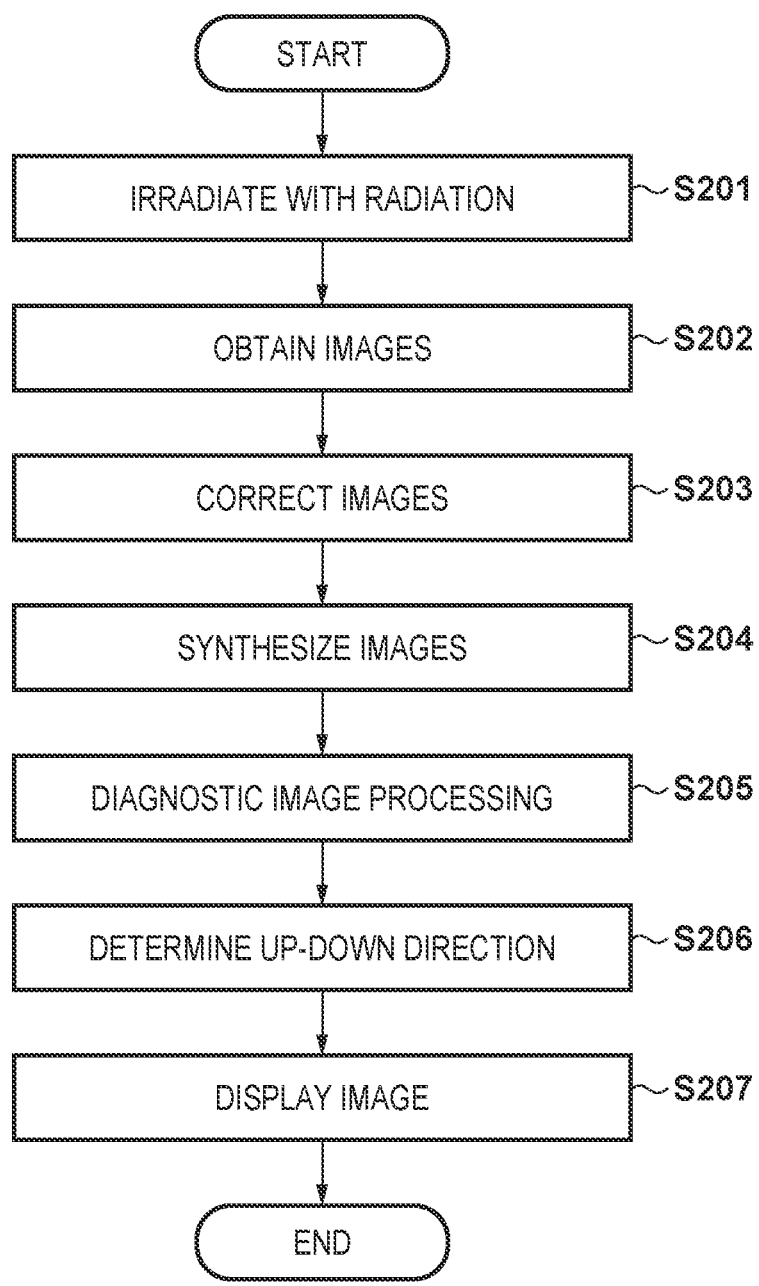
FIG. 2 is a flowchart showing a processing procedure in the radiation imaging apparatus according to the embodiment.
Figure 3:
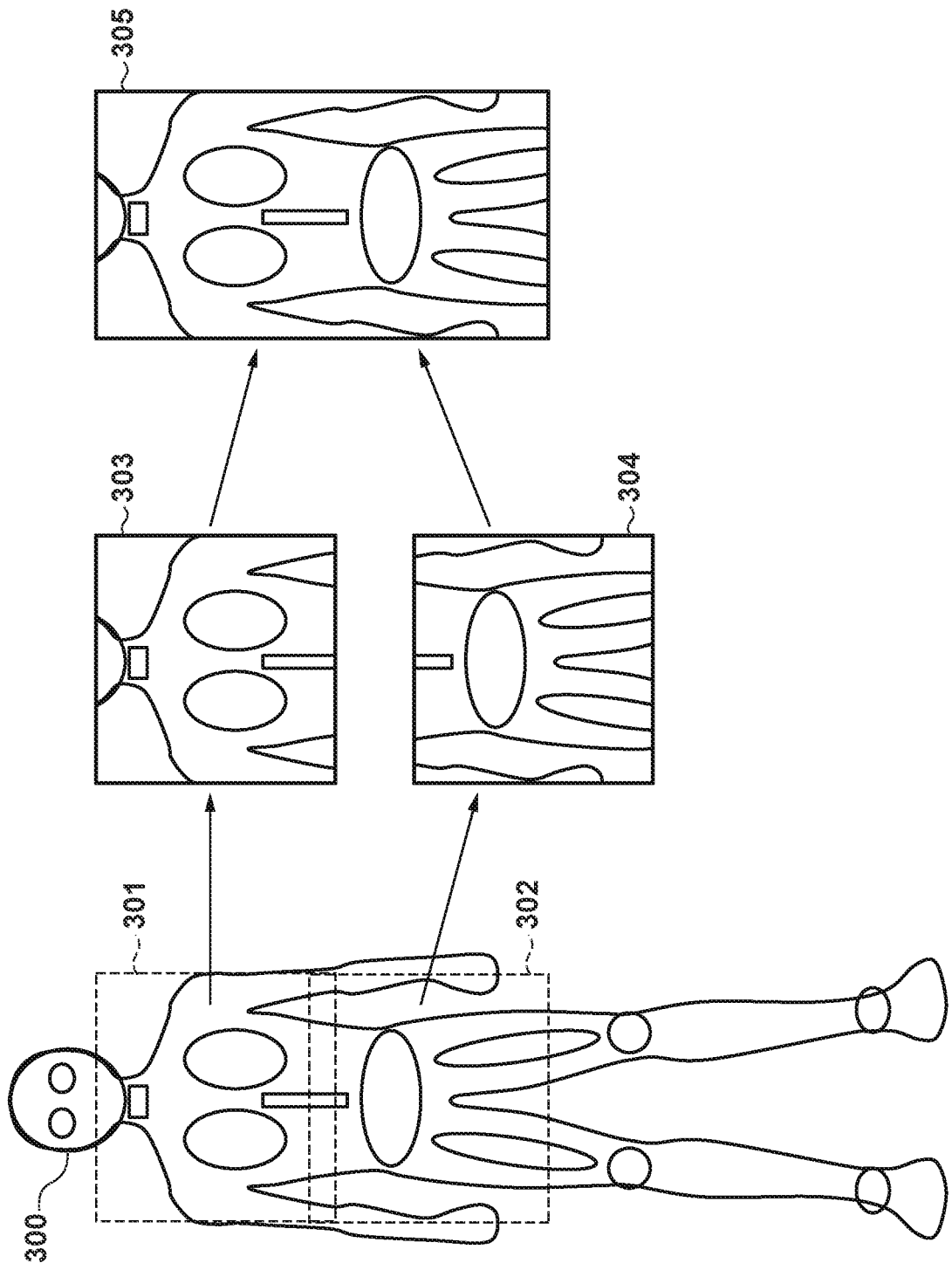
FIG. 3 is a view for explaining radiation images obtained from a plurality of radiation detectors and the generation of an elongated image.
Figure 4:
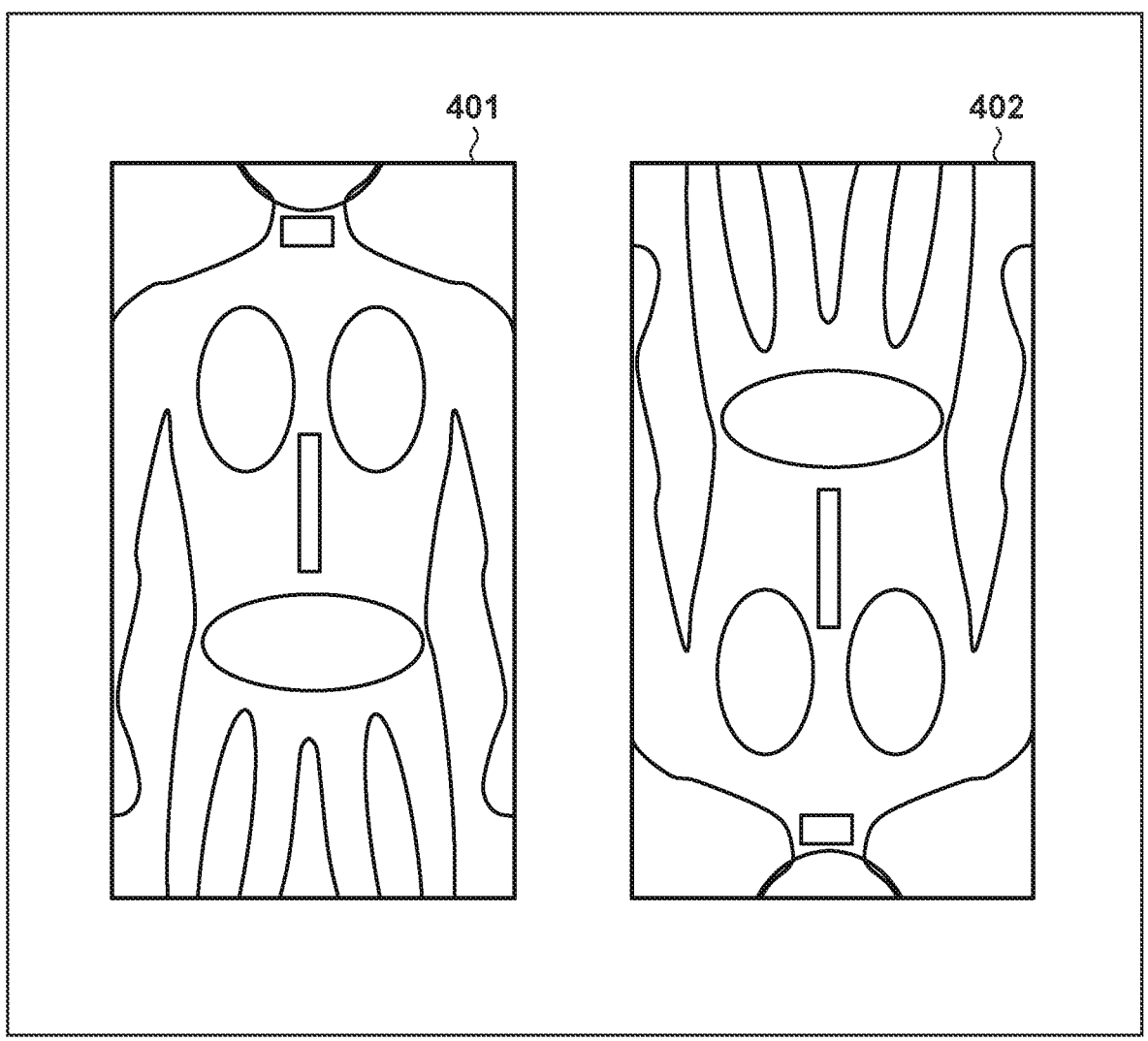
FIG. 4 is a view for explaining the up-down direction of an elongated image.

An imaging operation for an elongated image by the radiation imaging apparatus 100 having the above arrangement will be described in detail with reference to the flowchart of FIG. 2 and the schematic views of FIGS. 3 and 4.

In step S201, the radiation generator 104 drives the radiation generating unit 101 to irradiate the subject 103 with radiation. In this case, the radiation generator 104 generates radiation by supplying a high-voltage pulse to the radiation generating unit 101 in accordance with the pressing of the exposure switch (not shown).

In step S202, the FPD control units 105a and 105b respectively drive the FPDs 102a and 102b to obtain radiation images. In this case, upon irradiation with radiation, the FPDs 102a and 102b accumulate electric charge proportional to the doses of radiation in detection elements and output image data based on the accumulated electric charge. Upon receiving the image data from the FPDs 102a and 102b, the FPD control units 105a and 105b save the data as radiation images in the image saving unit 111 or the RAM 116. For example, as shown in FIG. 3, in radiation imaging aimed at a human body 300 as the subject 103, the FPD control unit 105a obtains a first radiation image 303 from the FPD 102a arranged in a first imaging range 301. The FPD control unit 105b obtains a second radiation image 304 from the FPD 102b arranged in a second imaging range 302.

In step S203, the image correction unit 120 performs image correction for the first radiation image 303 and the second radiation image 304 stored in the image saving unit 111 or the RAM 116. More specifically, the image correction unit 120 performs various types of correction processing, so-called preprocessing, such as offset correction, sensitivity correction, and defective pixel correction for correcting the characteristic variations of the solid-state image sensors which the FPDs 102a and 102b respectively include.

In step S204, the image synthesizing unit 121 synthesizes the first radiation image 303 and the second radiation image 304 having undergone image correction in step S203 into an elongated image 305. For example, the image synthesizing unit 121 decides the joining position between the first radiation image 303 and the second radiation image 304, and generates the elongated image 305 by joining the two images. Although the method of deciding a joining position is not specifically limited, for example, it is possible to decide a joining position based on separately obtained information concerning the relative position between the FPD 102a and the FPD 102b. Alternatively, it is possible to decide a joining position by applying an image analyzing technique such as template matching to the overlapping area between the first radiation image 303 and the second radiation image 304.

In step S205, the diagnostic image processing unit 122 applies diagnostic image processing to the elongated image 305 synthesized by the image synthesizing unit 121 in step S204. More specifically, the diagnostic image processing unit 122 performs gray level processing, dynamic range processing, and spatial frequency processing for the elongated image 305.

In step S206, the up-down direction determination unit 123 determines the up-down direction of the elongated image 305 synthesized in step S205. In this case, assume that an elongated image of a subject whose head region is oriented in the upward direction is regarded as an upward elongated image, and an elongated image of a subject whose head region is oriented in the downward direction is regarded as a downward elongated image. The elongated image 305 shown in FIG. 3 is an example of an upward elongated image. In this case, it is expected that displaying this elongated image in the upward direction as it is will implement image display suitable for diagnosis. However, depending on the placement of the subject 103 or the FPD 102, an elongated image may be oriented downward like an elongated image 402 shown in FIG. 4. In particular, in so-called supine position imaging of imaging the subject 103 placed on an imaging table, when imaging is performed in free directions without any limitation, an upward elongated image 401 and the downward elongated image 402 can appear at almost equal frequency. In order to always perform image display suitable for diagnosis in such a situation, it is necessary to display the elongated image 305 in a direction suitable for diagnosis upon determination of the up-down direction of the image. In this embodiment, the up-down direction determination unit 123 individually estimates the up-down direction of each of the first radiation image 303 and the second radiation image 304, and finally determines the up-down direction of the elongated image 305 based on the respective estimation results. The arrangement of the up-down direction determination unit 123 and its processing contents will be described in more detail later.

Subsequently, in step S207, the display unit 113 displays the elongated image 305 having undergone diagnostic image processing in step S205 in accordance with the up-down direction of the elongated image 305 determined in step S206. The processing in the radiation imaging apparatus 100 is then completed.

Figure 5:
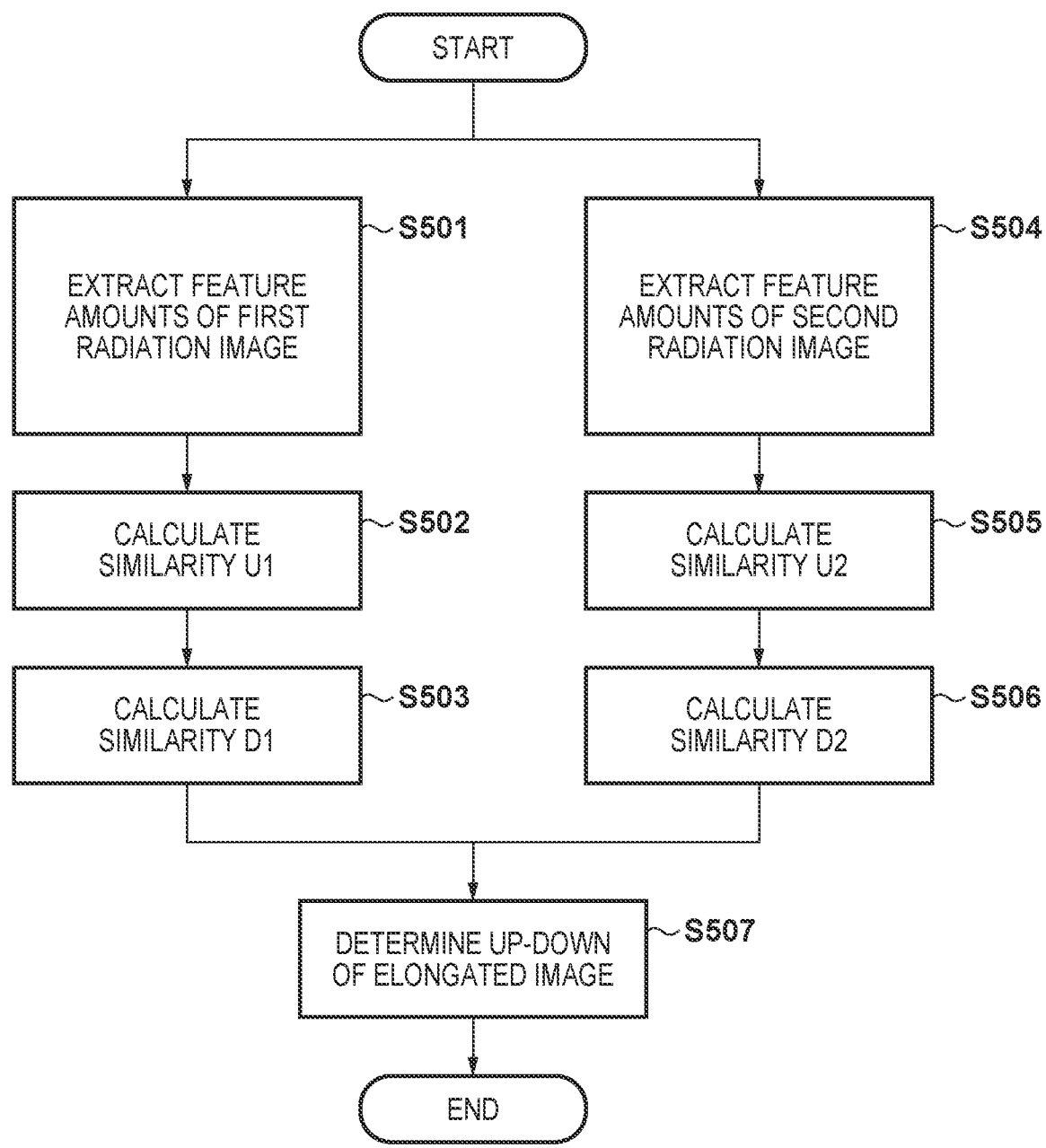
FIG. 5 is a flowchart showing a processing procedure in an up-down direction determination unit according to the first embodiment.
Figure 8:
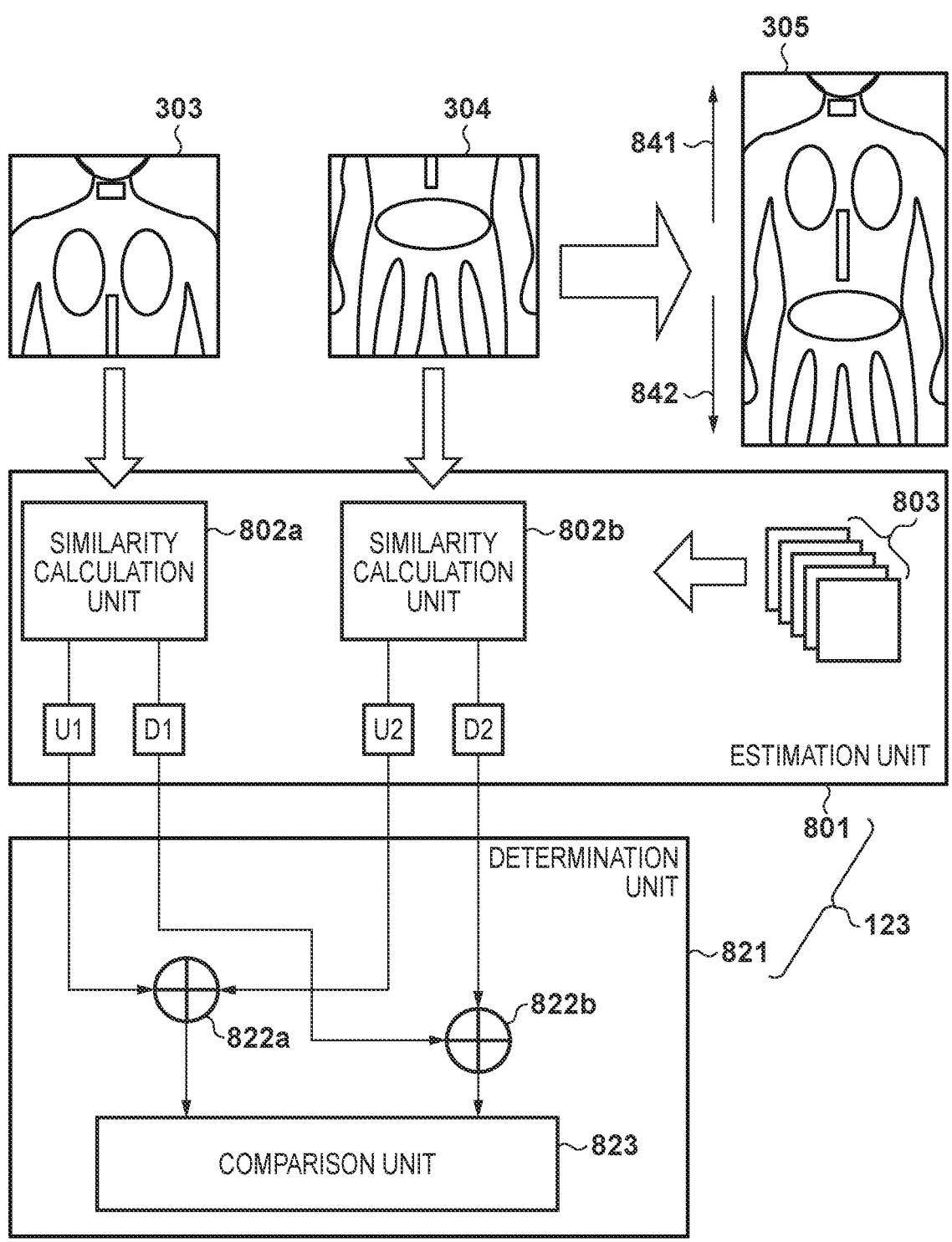
FIG. 8 is a block diagram showing the details of the up-down direction determination unit according to the first embodiment.

The up-down direction determination method using the up-down direction determination unit 123 in step S206 will be described in detail next with reference to the flowchart shown in FIG. 5 and the block diagram of FIG. 8. FIG. 5 is a flowchart showing up-down direction determination processing by the up-down direction determination unit 123 according to this embodiment. FIG. 8 is a block diagram showing the more detailed arrangement of the up-down direction determination unit 123 and its processing operation.

As shown in FIG. 8, the up-down direction determination unit 123 includes an estimation unit 801 and a determination unit 821. The estimation unit 801 estimates the up-down direction of each of a plurality of radiation images. The determination unit 821 determines the up-down direction of an elongated image based on the up-down direction estimation result concerning each of the plurality of radiation images which is obtained by the estimation unit 801. In order to determine the up-down direction of each image, for example, the direction of a subject in the image can be used. In this case, the estimation unit 801 estimates the direction of the subject in each of the plurality of radiation images. In addition, the determination unit 821 determines the direction of the subject in the elongated image based on the estimation result concerning each of the plurality of radiation images which is obtained by the estimation unit 801. As the direction of a subject in a radiation image and the direction of the subject in an elongated image, for example, it is possible to use the direction from the foot to the head of the subject or the direction from the head to the foot of the subject.

In this embodiment, the estimation unit 801 estimates a first possibility indicating the possibility of the direction of the head side of a subject in a radiation image being the first direction along the longitudinal direction of the elongated image 305, and a second possibility indicating the possibility of the direction of the head side of a subject being the second direction opposite to the first direction. More specifically, similarity calculation units 802a and 802b individually estimate the up-down direction possibilities (first and second possibilities) of the first radiation image 303 and the second radiation image 304. The determination unit 821 determines the direction of the subject (to be also referred to as the up-down direction of the image hereinafter) in the elongated image 305 based on the first possibility and the second possibility estimated concerning each radiation image by the estimation unit 801.

As described above, in the up-down direction determination unit 123, the estimation unit 801 and the determination unit 821 determine, based on the estimation result obtained by the estimation unit 801, whether a first direction 841 or a second direction 842 along the longitudinal direction of the elongated image 305 is the direction of the head side of the subject. FIG. 8 shows a state in which the first direction 841 is the direction of the head side. Assume that in the following description, when the direction of the head side of a subject is the first direction 841, the corresponding image is an upward image, and when the direction of the head side of a subject is the second direction 842, the corresponding image is a downward image. Although the method of estimating the up-down direction of a radiation image by the estimation unit 801 is not specifically limited, for example, the following estimation method can be used.

(1) Anatomical regions are detected from a radiation image, and the direction of the subject is estimated based on the likelihoods of the detected anatomical regions and the shapes or the relative positional relationship. For example, when the lung, heart, and liver are recognized as anatomical regions of a subject in a radiation image, the up-down direction of the radiation image is estimated based on the likelihood of the recognition of each region and at least the shape of each recognized region or the positional relationship between the respective regions.

(2) The possibility of a subject being in the first direction and the possibility of the subject being in the second direction are estimated by comparing the feature amounts of a radiation image with those of a plurality of reference images each as a teacher image in which the direction of the head side of the subject is known. More specifically, for example, it is possible to estimate the up-down direction of image data to be estimated by comparing the feature amounts of an image (to be referred to as a reference image hereinafter) in which the correct answer of the up-down direction is known in advance with those of the radiation image to be estimated. As feature amounts, for example, edge intensity, edge direction, and statistic amount of pixel values can be used.

(3) The up-down direction of each radiation image (the possibility of the first direction and the possibility of the second direction) is estimated by a machine learning method that has recently been popular. A supervised learning technique as one of the machine learning techniques is a technique of constructing a mechanism of outputting an up-down determination result upon inputting of the feature amounts of image data as a determination target by giving in advance a computer with a large amount of teacher image data constituted by combinations of the feature amounts of image data and the correct answers of the up-down directions and causing the computer to learn the data. In this case, the estimation unit 801 includes a determination device constructed by machine learning using a plurality of teacher images in each of which the direction of the subject is known. Inputting a radiation image to this determination device can obtain the first possibility indicating the possibility of the first direction and the second possibility indicating the possibility of the second direction.

A case in which the technique of (2) described above is used will be described below. The similarity calculation units 802a and 802b of the estimation unit 801 compare the feature amounts of the radiation images 303 and 304 with those of a plurality of reference images 803 in each of which the direction of the head side of the subject is known. The reference images 803 may be stored in, for example, the image saving unit 111. The similarity calculation units 802a and 802b calculate similarities U1 and U2 between the radiation images and upward reference images and similarities D1 and D2 between the radiation images and downward reference images. The estimation unit 801 uses the similarities U1 and U2 as indices each indicating the first possibility that the head side of the subject in the radiation image is the first direction along the longitudinal direction of the elongated image 305. The estimation unit 801 also uses the similarities D1 and D2 as indices each indicating the second possibility that the head side of the subject in the radiation image is the second direction opposite to the first direction.

The similarity calculation units 802a and 802b each divide a radiation image into a plurality of blocks and compare the feature amounts of the plurality of blocks with those of a corresponding block of each reference image 803, thereby calculating a similarity. First of all, in step S501, the similarity calculation unit 802a extracts the feature amounts of the first radiation image 303. More specifically, the similarity calculation unit 802a divides the radiation image 303 into a plurality of blocks each having a predetermined appropriate size and extracts, as feature amounts, for example, a statistic value (minimum, maximum, average, variance, or the like) of pixel values in each block and the intensity and direction of a representative edge of each block.

In step S502, the similarity calculation unit 802a calculates the similarity U1 between the feature amounts of the reference image 803 as an upward teacher image provided in advance as a correct answer with the feature amounts of the first radiation image 303. For example, the similarity calculation unit 802a calculates the similarity between the feature amounts of each block of the first radiation image 303 with those of a corresponding block of the reference image 803. The similarity calculation unit 802a then calculates the weighted sum of similarities for each block by applying a weight assigned in advance to each block and uses the calculated sum as the similarity U1. The similarity U1 can be used as an index indicating the likelihood (first possibility) of the first radiation image 303 being upward. In step S503, as in step S502, the similarity calculation unit 802a calculates the similarity D1 between the feature amounts of the reference image 803 as a downward teacher image provided in advance as a correct answer with the feature amounts of the first radiation image 303. The similarity D1 can be used as an index indicating the likelihood (second possibility) of the first radiation image 303 being downward.

Meanwhile, the similarity calculation unit 802b calculates the similarities U2 and D2 by executing processing similar to that in steps S501 to S503 with respect to the second radiation image 304 in steps S504 to S506. Referring to FIG. 5, the similarities (the similarities U1 and D1 and the similarities U2 and D2) are calculated in parallel concerning two radiation images. However, similarity calculation processing of two radiation images may be performed in series. In this case, the similarity calculation units 802a and 802b may be integrated into one unit. In addition, the processing sequence of processing for the first radiation image (steps S501 to S503) and processing for the second radiation image (steps S504 to S506) is not specifically limited. For example, it does not matter whether to perform first the processing for the first radiation image or the processing for the second radiation image data.

In step S507, the determination unit 821 determines the direction of the subject in the elongated image based on the result of integrating the first possibilities generated concerning the plurality of radiation images and the result of integrating the second possibilities generated concerning the plurality of radiation images. In this embodiment, the determination unit 821 determines the up-down direction of the elongated image 305 based on the similarities U1, D1, U2, and D2 calculated by the estimation unit 801 in steps S502, S503, S505, and S506. More specifically, for example, in the determination unit 821, an adder 822a calculates the sum of the similarities U1 and U2 as first possibility indices indicating the likelihoods of the first radiation image 303 and the second radiation image 304 being upward. In addition, an adder 822b calculates the sum of the similarities D1 and D2 as second possibility indices indicating the likelihoods of the first radiation image 303 and the second radiation image 304 being downward. A comparison unit 823 determines the up-down direction of the elongated image 305 by comparing the result (U1+U2) obtained from the adder 822a with the result (D1+D2) obtained from the adder 822b. That is, the comparison unit 823 determines the elongated image 305 as upward if U1+U2>D1+D2, and determines the elongated image 305 as downward if U1+U2≤D1+D2.

This embodiment has exemplified the arrangement configured to perform elongated imaging by using the two sets of the FPDs 102 and the FPD control units 105. Obviously, however, the embodiment can be applied to a case in which elongated imaging is performed by using three or more sets of such units. In addition, if a large number of reference images 803 impose a heavy processing load on the similarity calculation unit 802, the reference images to be compared with radiation images may be narrowed down. For example, the estimation unit 801 may use, for comparison (similarity calculation), reference images of the plurality of reference images 803 which exhibit matching degrees with the radiation images 303 and 304 equal to or more than a predetermined value. Alternatively, the estimation unit 801 may select reference images to be used for comparison based on an imaging regions detected from a radiation image as a comparison target upon classification of the reference images 803 according to imaging regions. A known method can be applied to a method of detecting an imaging region from a radiation image. Alternatively, an imaging region may be determined from the imaging instruction information provided from an information system such as an HIS or RIS to the radiation imaging apparatus 100 via a network. In addition, a radiation image and a reference image may be compared upon removal of a region from the radiation image which is not irradiated with radiation. A region which is not irradiated with radiation is a region generated mainly by a radiation aperture. A known method can be applied to this detection method.

As described above, according to the first embodiment, it is possible to accurately estimate the up-down direction of an elongated image in elongated imaging using a plurality of radiation imaging apparatuses. This makes it possible to provide the radiation imaging apparatus 100 that can display an elongated image in a direction suitable for diagnosis.

Second Embodiment

The first embodiment is configured to determine the up-down direction of a synthesized elongated image by using the results of calculating the possibilities of a plurality of radiation images (first and second radiation images) being upward and being downward. The second embodiment is configured to determine the up-down direction of an elongated image generated from a plurality of radiation images based on the results of calculating the possibilities of the elongated image being upward and downward in addition to the results of calculating the possibilities of each radiation image being upward and downward. That is, in the second embodiment, an estimation unit 801 estimates the direction of a subject in a radiation image and the direction of the subject in an elongated image 305 generated by an image synthesizing unit 121. A determination unit 821 then determines the direction of the subject in the elongated image 305, that is, the up-down direction of the elongated image based on the estimation results on a plurality of radiation images (for example, radiation images 303 and 304) and the elongated image by the estimation unit 801. Note that the arrangement of the radiation imaging apparatus 100 according to the second embodiment and its imaging operation for an elongated image are similar to those in the first embodiment (FIGS. 1 and 2). Up-down direction determination processing in step S206 will be described below.

In step S206, the up-down direction determination unit 123 regards the elongated image 305 as an up-down direction estimation target in addition to the first radiation image 303 and the second radiation image 304, and determines the up-down direction of the elongated image 305 based on estimation results on the respective images. Determination processing by the up-down direction determination unit 123 according to the second embodiment, that is, processing in step S206 will be described with reference to the flowchart shown in FIG. 6.

The up-down direction determination unit 123 calculates similarities U1 and D1 of the first radiation image 303 in steps S501 to S503, and calculates similarities U2 and D2 of the second radiation image 304 in steps S504 to S506. These processes are similar to those described in the first embodiment (FIG. 5). In steps S607 to S609, the estimation unit 801 of the up-down direction determination unit 123 executes processing similar to that in steps S501 to S503 with respect to the elongated image 305 to calculate a similarity U0 indicating the possibility of the elongated image 305 being upward and a similarity D0 indicating the possibility of the elongated image 305 being downward.

Figure 6:
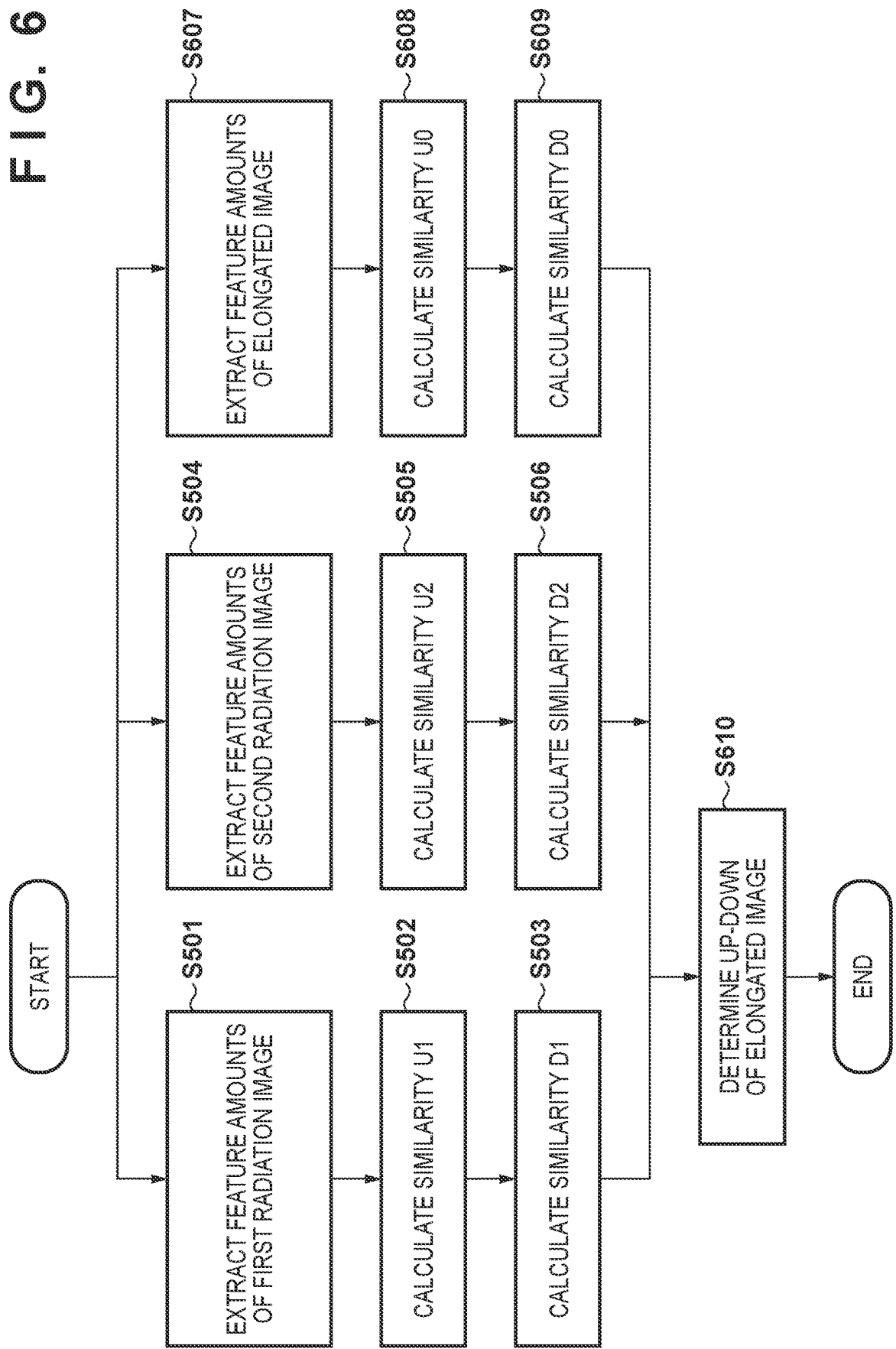
FIG. 6 is a flowchart showing a processing procedure in an up-down direction determination unit according to the second embodiment.

Referring to FIG. 6, the estimation unit 801 calculates similarities (the similarities U1 and D1, the similarities U2 and D2, and the similarities U0 and D0) concerning the three images (the first radiation image 303, the second radiation image 304, and the elongated image 305) in parallel. However, this is not exhaustive. The estimation unit 801 may perform calculation processing of the similarities of the three images in series. In this case, the processing sequence of processing for the first radiation image (steps S501 to S503), processing for the second radiation image (steps S504 to S506), and processing for the elongated image (steps S607 to S609) is not specifically limited. For example, it does not matter whether to perform first the processing for the first radiation image, the processing for the second radiation image, or the processing for the elongated image.

In step S610, the determination unit 821 of the up-down direction determination unit 123 determines the up-down direction of the elongated image 305 based on the similarities U1, D1, U2, D2, U0, and D0 calculated in steps S502, S503, S505, S506, S608, and S609. For example, the up-down direction determination unit 123 compares the sum of the similarities U1, U2, and U0 as indices indicating the likelihoods of the first radiation image 303, the second radiation image 304, and the elongated image 305 being upward with the sum of the similarities D1, D2, and D0 as indices indicating the likelihoods of the respective images being downward. The up-down direction determination unit 123 then determines the elongated image as upward if the sum of the similarities U1, U2, and U0 is large, and determines the elongated image as downward if otherwise.

As described above, according to the second embodiment, it is possible to accurately estimate the direction of a subject in an elongated image (the up-down direction of the elongated image) in elongated imaging using a plurality of radiation detectors. This makes it possible to provide the radiation imaging apparatus 100 that can display an elongated image in an up-down direction suitable for diagnosis.

Third Embodiment

Figure 7:
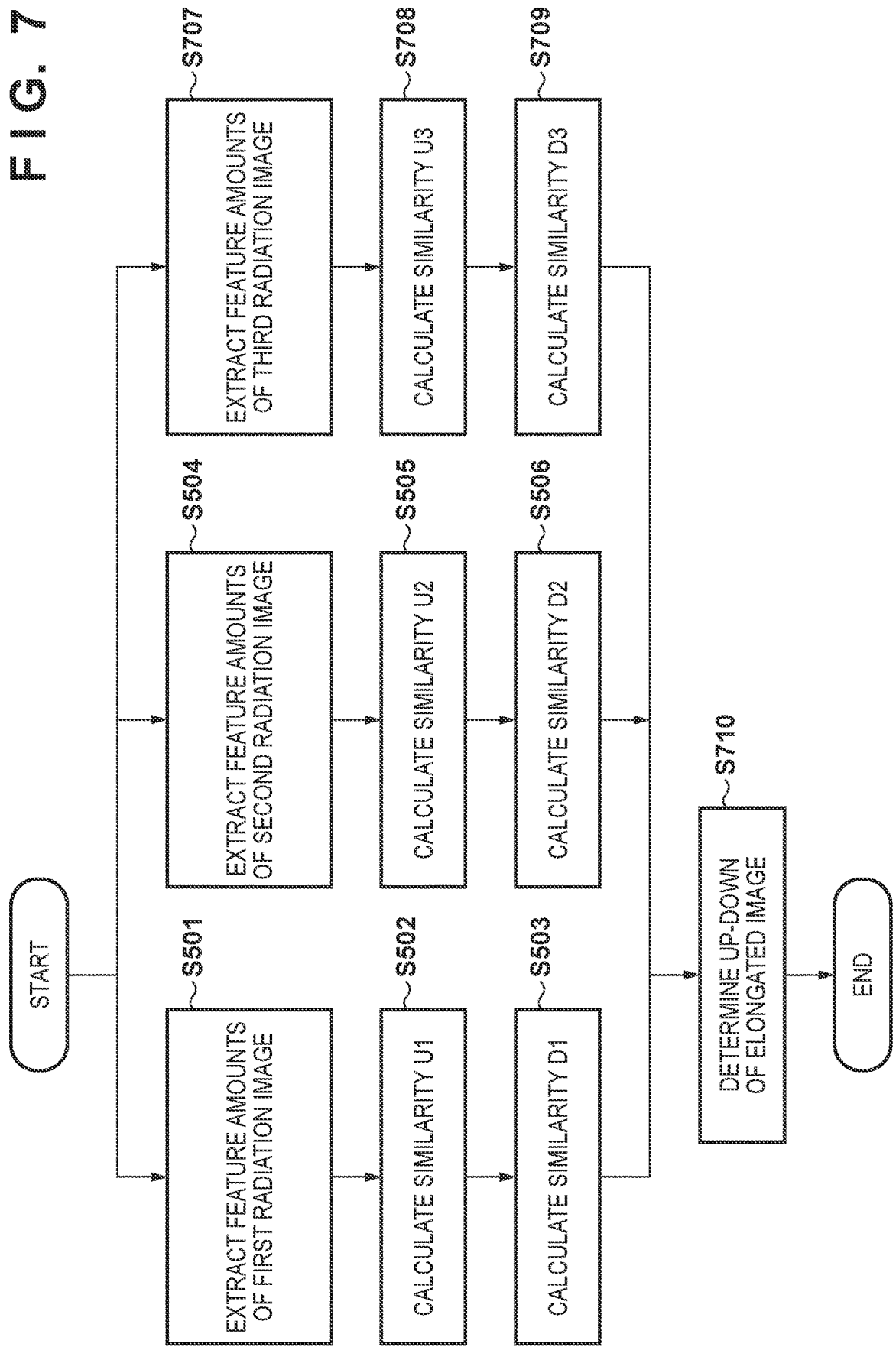
FIG. 7 is a flowchart showing a processing procedure in an up-down direction determination unit according to the third embodiment.
Figure 9:
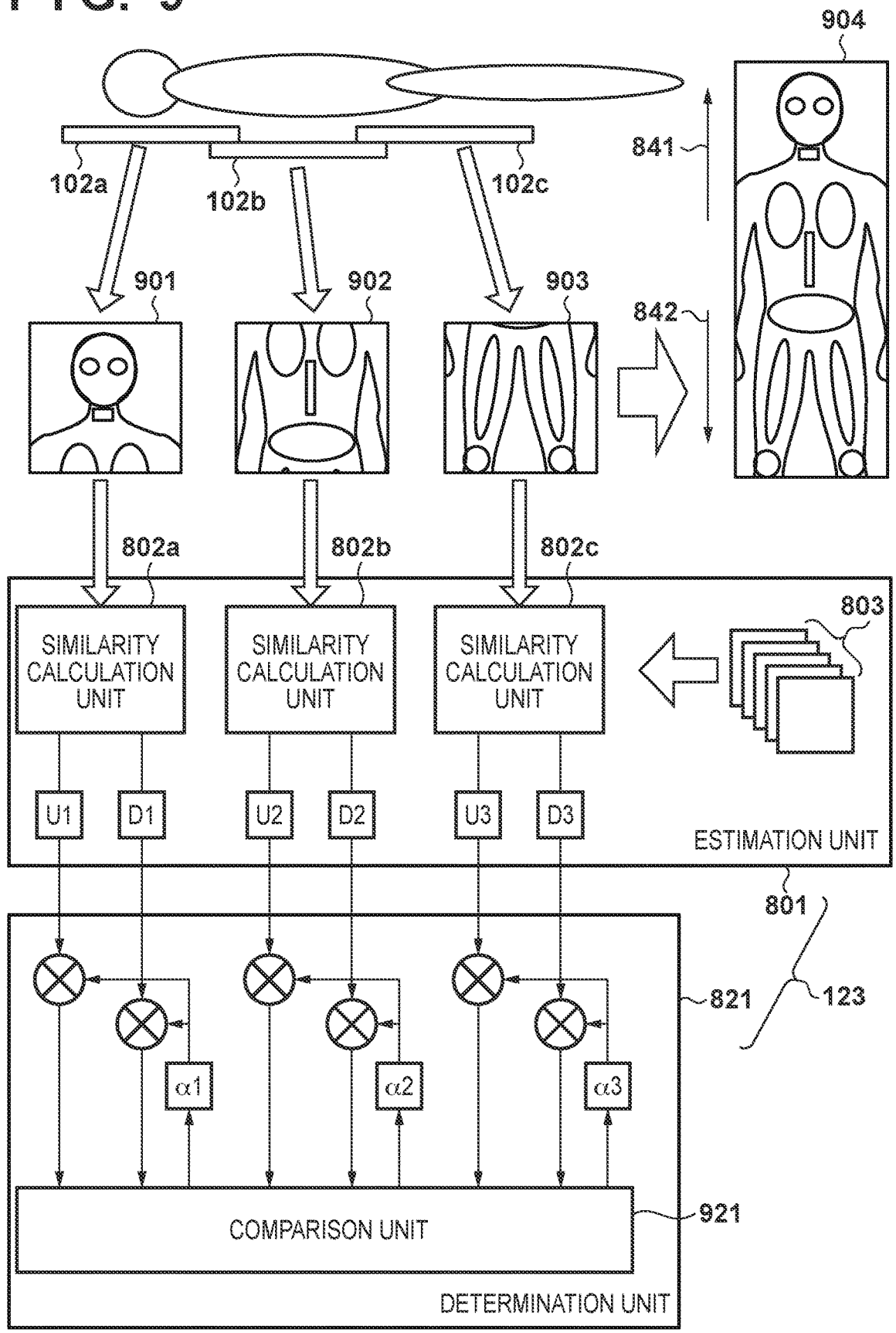
FIG. 9 is a block diagram showing the details of the up-down direction determination unit according to the third embodiment.

The third embodiment will exemplify an arrangement configured to perform elongated imaging by using three sets of FPDs 102 and FPD control units 105. FIG. 7 is a flowchart showing up-down direction determination processing according to the third embodiment. FIG. 9 is a block diagram for explaining the detailed arrangement of an up-down direction determination unit 123 and its up-down direction determination processing. The third embodiment will exemplify an arrangement including three FPDs 102a to 102c and FPD control units 105a to 105c.

As in the first embodiment, in step S206, the up-down direction determination unit 123 determines the up-down direction of an elongated image 904. The third embodiment is configured to determine an up-down direction based on a first radiation image 901, a second radiation image 902, and a third radiation image 903. That is, a determination unit 821 applies weights to the first and second possibilities described above based on the relative positional relationship between the FPDs 102a to 102c as the plurality of radiation detectors that have obtained the plurality of radiation images 901 to 903. Assume that the FPDs 102a to 102c that obtain the radiation images 901 to 903 are arranged side by side along the longitudinal direction of the elongated image 904, as shown in FIG. 9. In this case, the determination unit 821 applies a larger weight to the similarity calculated concerning a radiation image from the FPD 102b arranged in the middle than to the similarities calculated concerning radiation images from the FPDs 102a and 102c arranged at end portions.

First of all, in steps S501 to S503, a similarity calculation unit 802a of the up-down direction determination unit 123 calculates similarities U1 and D1 of the first radiation image 901. In steps S504 to S506, a similarity calculation unit 802b of the up-down direction determination unit 123 calculates similarities U2 and D2 of the second radiation image 902. These processes are similar to those in steps S501 to S506 in the first embodiment (FIG. 5). In steps S707 to S709, the similarity calculation unit 802c calculates similarities U3 and D3 by executing processing similar to that in steps S501 to S503 with respect to the third radiation image 903.

Referring to FIG. 7, the calculation units calculate the similarities (the similarities U1 and D1, the similarities U2 and D2, and the similarities U3 and D3) concerning the three radiation images in parallel. However, the calculation units may perform calculation processing of the similarities of the three images in series. In this case, the processing sequence of processing for the first radiation image 901 (steps S501 to S503), processing for the second radiation image 902 (steps S504 to S506), and processing for the third radiation image 903 (steps S707 to S709) is not specifically limited. It does not matter whether to perform first the processing for the first radiation image, the processing for the second radiation image, or the processing for the third radiation image. In addition, the number of radiation images (the number of radiation detectors) may be three or more.

In step S710, the determination unit 821 determines the up-down direction of an elongated image 305 based on the similarities U1, D1, U2, D2, U3, and D3 calculated in steps S502, S503, S505, S506, S708, and S709. In this case, the determination unit 821 determines, based on the relative positional relationship between the plurality of radiation detectors (FPDs 102a to 102c) that have obtained the plurality of radiation images, the direction of the subject in the image by applying weights to possibilities (similarities) estimated by an estimation unit 801. As described above, in this case, the determination unit 821 applies a larger weight to the radiation image obtained from the radiation detector arranged in the middle than to the radiation images obtained from the radiation detectors arranged at end portions. When, for example, the FPD 102b is arranged in the middle, it is expected that a second radiation image 304 obtained from the FPD 102b reliably includes the subject and is rich in information for estimating an up-down direction. This makes it possible to improve determination accuracy by using a determination method (for example, a method with weighting) with higher importance being placed on image data than on other image data as follows.

The determination unit 821 multiplies the similarities U1 and D1 output from the similarity calculation unit 802a by a weight $\alpha 1$, multiplies the similarities U2 and D2 output from the similarity calculation unit 802b by a weight $\alpha 2$, and multiplies the similarities U3 and D3 output from the similarity calculation unit 802c by a weight $\alpha 3$. A comparison unit 921 integrates weighted similarities and determines the up-down direction of the elongated image 904 as follows:

If $U1 \times \alpha 1 + U2 \times \alpha 2 > D1 \times \alpha 1 + D2 \times \alpha 2$, the upward direction is determined.

If $U1 \times \alpha 1 + U2 \times \alpha 2 \leq D1 \times \alpha 1 + D2 \times \alpha 2$, the downward direction is determined.

If, for example, the weights $\alpha 1$ and $\alpha 3$ are set to 1 and the weight $\alpha 2$ is set to 2, the comparison unit 921 determines the up-down direction of the elongated image 904 as follows:

If $U1 + U2 \times 2 + U3 > D1 + D2 \times 2 + D3$, the upward direction is determined.

If $U1 + U2 \times 2 + U3 \leq D1 + D2 \times 2 + D3$, the downward direction is determined.

In the third embodiment, weights are decided based on the relative positional relationship between the radiation detectors. However, this is not exhaustive. For example, the determination unit 821 may detect a region of a radiation image which is not irradiated with radiation, and determine the direction of a subject in an elongated image upon reducing a weight to be applied to an estimation result with an increase in the size of the detected region. In this case, a region which is not irradiated with radiation is a region which is not irradiated with radiation due to, for example, a radiation aperture. Such regions can be detected by a known method. In addition, alternatively, the determination unit 821 may determine the direction of a subject in an elongated image upon increasing a weight to be applied to an estimation result concerning a radiation image with an increase in the number of feature amounts extracted from the radiation image. Furthermore, alternatively, the determination unit 821 may determine a region of a substance in each radiation image and the direction of the subject in an elongated image by applying a weight corresponding to each determined region to an estimation result on each of a plurality of radiation images. In this case, for example, a large weight is applied to an estimation result on a radiation image in which an imaging region is determined as a head region, and a small weight is applied to an estimation result on a radiation image in which an imaging region is determined as a leg region. Note that a known method can be used to determine an imaging region in a radiation image. Alternatively, an imaging region may be determined from the imaging instruction information provided from an information system such as an HIS or RIS to a radiation imaging apparatus 100 via a network As described above, according to the third embodiment, it is possible to accurately estimate the up-down direction of an elongated image by considering the placement of FPDs in elongated imaging using a plurality of radiation detectors. According to the third embodiment, this makes it possible to provide a radiation imaging system that can perform screen display in an up-down direction suitable for diagnosis.

According to the present invention, it is possible to accurately determine the direction of a subject in an elongated image obtained by elongated imaging using a plurality of radiation detectors.

Other Embodiments

Embodiment(s) of the present invention can also be realized by a computer of a system or apparatus that reads out and executes computer executable instructions (e.g., one or more programs) recorded on a storage medium (which may also be referred to more fully as 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
an obtaining unit configured to obtain a plurality of radiation images generated by causing a plurality of radiation detectors to detect radiation with which a subject is irradiated;
a synthesizing unit configured to generate an elongated image by synthesizing the plurality of radiation images;
an estimation unit configured to estimate a direction of the subject in each of the plurality of radiation images; and
a determination unit configured to determine a direction of the subject in the elongated image based on a direction estimation result obtained by the estimation unit on each of the plurality of radiation images.

2. The image processing apparatus according to claim 1, wherein the determination unit determines a direction from a head side to a foot side of the subject in the elongated image.

3. The image processing apparatus according to claim 1, wherein the estimation unit estimates a direction from a head side to a foot side of a subject with respect to each of the plurality of radiation images.

4. The image processing apparatus according to claim 1, wherein the estimation unit estimates a first possibility indicating a possibility of a direction of a head side of a subject in a radiation image being a first direction along a longitudinal direction of the elongated image and a second possibility indicating a possibility of the direction of the head side being a second direction opposite to the first direction, and
the determination unit determines a direction of a subject in the elongated image based on the first possibility and the second possibility estimated with respect to each of the plurality of radiation images.

5. The image processing apparatus according to claim 4, wherein the determination unit determines a direction of a subject in the elongated image based on a result of integrating the first possibilities generated concerning the plurality of radiation images and a result of integrating the second possibilities generated concerning the plurality of radiation images.

6. The image processing apparatus according to claim 1, wherein the estimation unit estimates a direction of a subject in the elongated image generated by the synthesizing unit, and
the determination unit determines a direction of a subject in the elongated image based on estimation results obtained by the estimation unit concerning the plurality of radiation images and the elongated image.

7. The image processing apparatus according to claim 6, wherein the estimation unit estimates first possibilities indicating possibilities of a direction of a head side of a subject being a first direction along a longitudinal direction of the elongated image with respect to the plurality of radiation images and the elongated image and second possibilities indicating possibilities of the direction of the head side being a second direction opposite to the first direction, and
the determination unit determines a direction of a subject in the elongated image based on the first possibilities and the second possibilities estimated concerning the plurality of radiation images and the elongated image.

8. The image processing apparatus according to claim 4, wherein the estimation unit estimates the first possibilities and the second possibilities by comparing a feature amount of a radiation image with feature amounts of a plurality of reference images in which a direction of a head side of a subject is known.

9. The image processing apparatus according to claim 8, wherein the estimation unit divides the radiation image into a plurality of blocks and compares a feature amount of each of the plurality of blocks with a feature amount of a corresponding block of a reference image.

10. The image processing apparatus according to claim 8, further comprising a detection unit configured to detect a region of the radiation image which is not irradiated with radiation,
   wherein that the estimation unit performs the comparison upon removal of a region detected by the detection unit.

11. The image processing apparatus according to claim 8, wherein the estimation unit uses, for the comparison, a reference image, of a plurality of reference images, which exhibits a matching degree not less than a predetermined value with respect to the radiation image.

12. The image processing apparatus according to claim 1, wherein the estimation unit detects anatomical regions from a radiation image and estimates a direction of the subject based on likelihoods of detected anatomical regions and shapes of the detected anatomical regions or a relative positional relationship between the detected anatomical regions.

13. The image processing apparatus according to claim 1, wherein the estimation unit includes a determination device constructed by machine learning using a plurality of teacher images in which a direction of a subject is known.

14. The image processing apparatus according to claim 1, wherein the determination unit determines a direction of the subject by applying a weight to an estimation result by the estimation unit based on a relative positional relationship between the plurality of radiation detectors that have obtained the plurality of radiation images.

15. The image processing apparatus according to claim 1, further comprising a detection unit configured to detect a region of a radiation image which is not irradiated with radiation,
   wherein the determination unit determines a direction of a subject in the elongated image upon reducing a weight to be applied to an estimation result concerning a radiation image with an increase in a region of the radiation image which is detected by the detection unit.

16. The image processing apparatus according to claim 1, wherein the determination unit determines a direction of a subject in the elongated image upon increasing a weight to be applied to an estimation result concerning a radiation image with an increase in the number of feature amounts extracted from the radiation image.

17. The image processing apparatus according to claim 1, wherein the determination unit determines a region of a subject in a radiation image and determines a direction of a subject in the elongated image by applying a weight corresponding to the determined region to an estimation result on each of the plurality of radiation images.

18. The image processing apparatus according to claim 1, further comprising a display control unit configured to display the elongated image on a display unit based on a direction of a subject determined by the determination unit.

19. An image determination method comprising:
   obtaining a plurality of radiation images by detecting radiation with which a subject is irradiated;
   generating an elongated image by synthesizing the plurality of radiation images;
   estimating a direction of the subject in each of the plurality of radiation images; and
   determining a direction of the subject in the elongated image based on a direction estimation result obtained in the estimating on each of the plurality of radiation images.

20. A non-transitory computer-readable storage medium storing a program for causing a computer to execute an image determination method comprising:
   obtaining a plurality of radiation images by detecting radiation with which a subject is irradiated;
   generating an elongated image by synthesizing the plurality of radiation images;
   estimating a direction of the subject in each of the plurality of radiation images; and
   determining a direction of the subject in the elongated image based on a direction estimation result obtained in the estimating on each of the plurality of radiation images.

* * * * *